United States Patent [19]
Ho et al.

[11] Patent Number: 6,040,171
[45] Date of Patent: Mar. 21, 2000

[54] APPARATUS FOR ANALYZING BIOLOGICAL SAMPLES

[75] Inventors: Zonh-Zen Ho, Hacienda Heights; Tomasz P. Jannson, Torrance; Robert A. Lieberman, Torrance; Gajendra D. Savant, Torrance; Allan Wang, Torrance, all of Calif.

[73] Assignee: Physical Optics Corporation, Torrance, Calif.

[21] Appl. No.: 09/138,240

[22] Filed: Aug. 21, 1998

[51] Int. Cl.⁷ .................................................. C12M 3/00
[52] U.S. Cl. ................................... 435/288.1; 435/288.3; 435/299.2; 435/304.1; 435/305.1; 422/102; 356/244; 356/246
[58] Field of Search ..................... 422/102; 435/288.1, 435/288.3, 299.2, 304.1, 305.1; 356/244, 246

[56] References Cited

U.S. PATENT DOCUMENTS

| | | | |
|---|---|---|---|
| 4,245,042 | 1/1981 | Weinstein et al. | 435/30 |
| 4,741,619 | 5/1988 | Humphries et al. | 356/246 |
| 5,272,084 | 12/1993 | O'Connell et al. | 435/240.243 |
| 5,294,551 | 3/1994 | Furcht et al. | . |
| 5,365,354 | 11/1994 | Jannson et al. | 359/15 |
| 5,496,502 | 3/1996 | Thomson | 252/301.17 |
| 5,534,386 | 7/1996 | Petersen et al. | 430/320 |
| 5,602,029 | 2/1997 | Miyamoto | 435/395 |
| 5,609,939 | 3/1997 | Petersen et al. | 428/141 |

OTHER PUBLICATIONS

Davis, J.M., *Basic Cell Culture,* Oxford University Press, New York, 1994, pp. 17–18 & pp. 108–121.
Folkman, J. & Moscona, A. "Role of Cell Shape in Growth Control." *Nature,* vol. 273, Jun. 1, 1978, pp. 345–349.
Freshney, R. Ian, *Culture of Animal Cells,* 3rd ed., Wiley–Liss, New York, 1994, pp. 71–79.
Ireland, G.W., et al. "Limitation of Substratum Size Alters Cytoskeletal Organization & Behaviour of Swiss 3T3 Fibroblasts." *Cell Biol. Int. Rep.,* vol. 13, No. 9, Sep. 1989, pp. 781–790.
Shiba, Y. & Kanno, Y. "Modulation of Survival & Proliferation of BSC–1 Cells Through Changes in Spreading Behavior Caused by the Tumor–Promoting Phorbol Ester TPA." *Cell Struct. Funct.* 14, 1989, pp. 685–696.
Singhvi, R., et al. "Engineering Cell Shape and Function." *Science,* vol. 264, Apr. 29, 1994, pp. 696–698.
St. John, P.M., et al. "Preferential Glial Cell Attachment to Microcontact Printed Surfaces." *Journal of Neuroscience Methods,* 75, 1997, pp. 171–177.

*Primary Examiner*—David A. Redding
*Attorney, Agent, or Firm*—Nilles & Nilles, S.C.

[57] ABSTRACT

Apparatus for analyzing biological samples includes a unique surface which promotes adhesion, growth and optical analysis of samples. The unique surface is formed at the bottom of each well of a microplate and provides increased surface area with a distribution of features operative also to shape and redirect light used to sense test results. The unique surface may be used in forms such as a monolith, a microplate, a chamber, a flask and others.

12 Claims, 3 Drawing Sheets

APPARATUS FOR ANALYZING BIOLOGICAL SAMPLES

FIELD OF THE INVENTION

This invention relates to apparatus for cell culture and for immunological testing and the like employing, for example, microplates.

BACKGROUND OF THE INVENTION

Apparatus for cell culture and for immunological testing is commercially available and in wide spread use. One familiar such apparatus is known as a microplate typically comprising a substrate or base plate to which is connected an array of upstanding wells.

It has long been appreciated that an increase in the surface area of the exposed portion of the surface of the substrate at the bottom of each well would be beneficial in increasing the speed at which cell growth occurs in the well. Obtaining such an increase in surface area becomes an increasingly challenging problem as the number of wells per unit area of the base plate increases.

It also has long been appreciated that the surface of the base plate or substrate is important for cell attachment and coatings to this end also are available commercially.

It also has been long appreciated that the optical properties of the materials used in such apparatus are important because the results of tests from such apparatus are determined optically either by reflected light or by light transmitted through the base plate.

The speed at which cell cultures grow and morphology of cultured cells are important in the laboratory, in the clinic and in biotechnology and medical industries. Unfortunately, materials, coatings, well configurations and base plate surface textures often are incompatible and invariably lead to a diminution of optical properties as well as other adverse effects.

SUMMARY OF THE INVENTION

A primary object of the invention is to provide apparatus for analyzing biological samples. The apparatus includes a container having a surface that redirects light incident thereto into a controlled pattern with smooth brightness variation. In accordance with a first aspect of the invention, this primary object is achieved by using apparatus having a base plate and side walls for forming a receptacle for the biological sample. The base plate has a surface for receiving the sample. The surface has a distribution of features that operate to redirect light incident thereto into a controlled pattern with smooth brightness variation.

Another object of the invention is to provide an apparatus for enhanced cell growth. In accordance with this aspect of the invention, the features on the surface have a feature size about equal to the mean size of the cells, and the features are randomly distributed.

Still another object of the invention is to provide an apparatus having a plurality of receptacles for cells. In accordance with still another object of the invention, the apparatus includes an array of upstanding wells connected to the surface with each well exposing a portion of the surface.

Another primary object of the invention is to provide apparatus for analyzing biological samples in which the apparatus is a container. In accordance with this aspect of the invention, this primary object is achieved by providing apparatus having a container including a base plate and side walls for forming a receptacle for the sample. The base plate has a surface for receiving a sample, with the surface having a distribution of features having lateral dimensions about equal to the mean size of cells, and the features redirect light incident thereto in a controlled pattern with smooth brightness variation.

Other objects, features, and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE INVENTION

Figure 1:
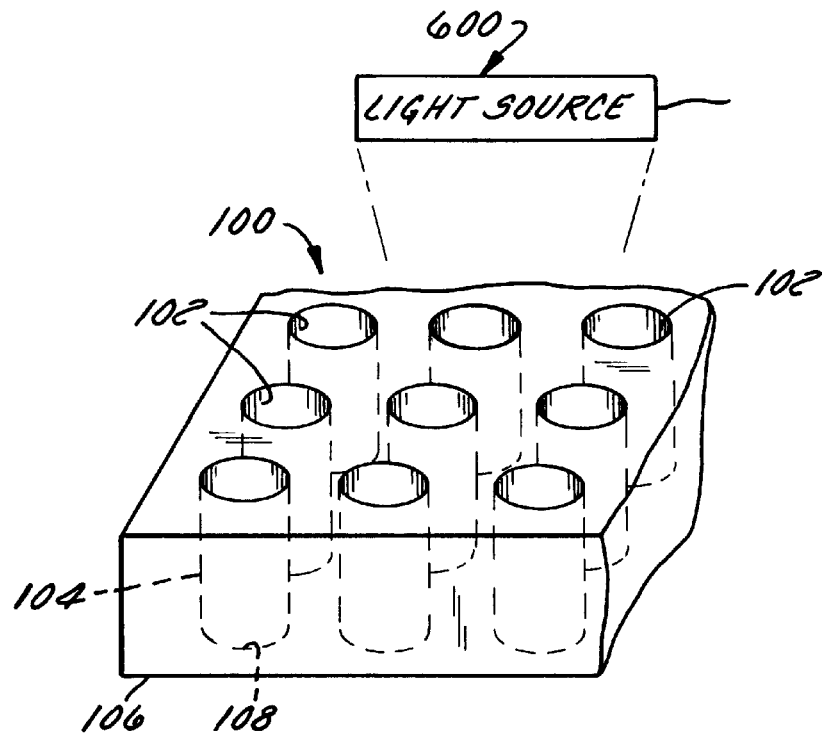
FIG. 1 is a perspective view of a portion of an analysis apparatus (i.e., a microplate) in accordance with the principles of this invention.

In accordance with the principles of this invention, the optical diffuser disclosed in U.S. Pat. No. 's 5,365,354, 5,534,386 and 5,609,939 to Physical Optics Corporation of Torrance, California has been found not only to provide enhanced optical properties for cell culture and immunological testing apparatus but, surprisingly, to provide significantly enhanced speed of cell growth and improved cell morphology in cell cultures. Additionally, significant signal or speed enhancement also occurs in immunological tests performed with such apparatus.

In one specific embodiment a commercial microplate about three by six inches on a side and having ninety-six upstanding wells had the bottom platform removed and a substitute platform with an "optical diffuser" surface made as disclosed in the above-noted patents. The so-modified microplate was tested and achieved cell adhesion that was significantly better (i.e., an order of magnitude better) than uncoated, commercially available microplates; cultured cells also exhibited virtually perfect cell formation. This result provides significant advantages for pharmaceutical and for diagnostic and clinical determinations.

Other so-modified microplates were used to perform enzyme-linked immunosorbent assay (ELISA) tests and showed signal strengths two to three times greater than unmodified microplates.

The invention is based on the recognition that the light diffuser of the above-identified patents not only provided improved light reflection and transmission but it did so with a material compatible with microplate requirements and provided a substrate feature size which increased substrate surface area while doing so.

Diffusers with a feature size in the test apparatus that was approximately about the same as the cell size for cultures tested provided significant advantages for cell culture. Diffuser structures with properly chosen feature size were also shown to significantly enhance signal strength in ELISA tests.

Tests for cell culture or for immunological testing carried out using such microplates and other structures were found to produce results consistently comparable or better than the quite costly coated plates but at a cost commensurate with the lowest cost microplate.

The cell growth benefits achieved by using the light diffuser surface also are achieved in the dark. Consequently, it appears to be the mechanical size and distribution of the surface features which contribute to those benefits. For immunoassay applications, the increased surface area of the diffuser structure appears to provide increased reagent packing density thus the size and distribution of these features contributes to the benefits to immunoassay as well. The fact that those features are formed in a manner to shape light (reflected or transmitted) advantageously contributes to the read out of the results.

It should be understood that the benefits desired from the use of a "diffuser" surface are achieved also with apparatus such as flasks and not just microplates.

DETAILED DESCRIPTION OF EMBODIMENTS OF THE INVENTION

Figure 2:
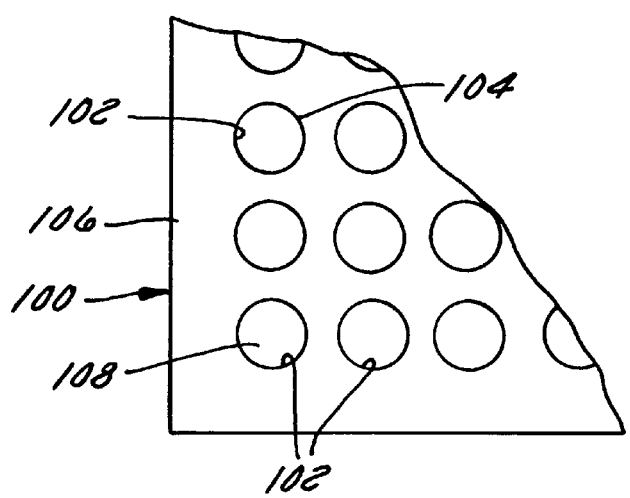
FIG. 2 is a top view of the apparatus of FIG. 1.

In view of the foregoing, and with references to FIG. 1 and FIG. 2, a microplate 100 includes a plurality of analysis wells 102. Each analysis well 102 has a generally cylindrical sidewall 104 extending above a substantially planar substrate or base plate 106 defining a bottom 108. Microplate 100 is preferably formed from a plastic material such as polystyrene, polycarbonate, polyvinylchloride (PVC) or the like chosen for its optical transmission properties. Microplate 100 may be formed to include a number of analysis wells 102 with analysis wells being shown in FIG. 1 for purposes of illustrating the present invention.

Figure 3:
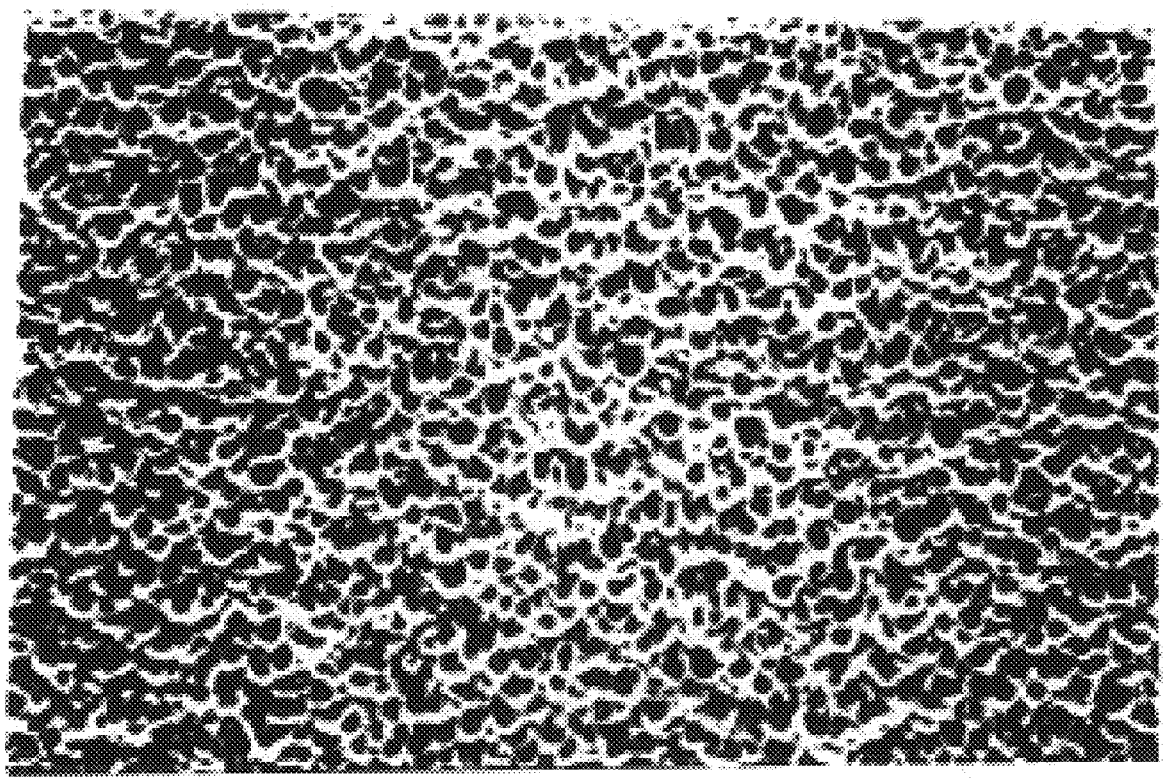
FIG. 3 is a perspective view of the base plate of the apparatus of FIG. 2.

It has been found that a three-dimensional structure utilized in diffuser technology, such as the diffuser structures disclosed in U.S. Pat. Nos. 5,365,354, 5,534,386 and 5,609,939 the disclosures of which are hereby expressly incorporated herein by references, provide an unexpectedly sample friendly environment. As described therein, a three-dimensional light shaping structure comprising random, disordered, and non-planar speckle may be recorded and developed in a photosensitive medium so that the medium has non discontinuous and smoothly varying changes in its refractive index (e.g., a gradient refractive index) which scatter collimated light into a controlled pattern with smooth brightness variation. A three-dimensional surface structure formed in this manner may be replicated in any number of materials, transparent or nontransparent, and then be adapted to form bottom 108. Such a bottom having three-dimensional surface structures is shown in FIG. 3.

Although the resultant microplate visually is virtually indistinguishable from prior art microplates and is used in exactly the same way, improved speed of cell development and cell morphology results and enhanced immunological results occur.

An important characteristics of the three-dimensional surface structure is the aspect ratio, i.e., the ratio of the height to the width of the surface structures. For example, an aspect ratio in the range of 1:3 (height to width) may be used with an aspect ratio of approximately 1:2 being preferred for growing certain cell types. Other larger or smaller aspect ratios may be used, but manufacturing limitations currently limit larger aspect ratios. A preferred arrangement may utilize surface structures on the order of about 1–5 microns high by 2–10 microns wide for cells but preferably smaller for molecules. Larger or smaller structures may be used. For enhancing performance in ELISA or other assays, optimal surface structure is dependent on the sample, and the aspect ratio is selected to maximize surface area for the sample of interest, while retaining beneficial optical properties. Such control and optimization of the surface structure and surface area was heretofore not possible. Moreover, the three-dimensional surface structure may be formed with a substantially random orientation that is beneficial to cell growth and assay uniformity.

The invention relates to an innovative substrate for biological, medical, and other applications. The innovative three-dimensional structure can be fabricated or formed on any substrate for use in (1) cell-based assays, (2) bioassays, and (3) concentrations of cells and molecules. The three-dimensional structure increases surface area and enhances the optical properties of the substrate. The substrate can be shaped into a suitable form including a slide, strip, plate, dish, flask, or sheet. Many techniques, such as injection molding, compression molding, laser or electronic beam writing, and mechanical processes can be used to transfer the microstructure onto the substrate.

When biological cells are applied to the three-dimensional structure on a substrate, the cells not only bind tightly onto the structure, but also present an improved morphology. Additionally, the adhesion of the cells to the substrate is increased. The innovative substrate shows more cells remaining on the surface after washing than in any of the existing commercial substrates. The innovative substrate's three-dimensional structure roughens the substrate's surface, improves cell morphology, creates a large surface area thereby increasing cell density, increases cell adhesion, and creates an environment highly suitable for cell growth. Cells grow rapidly in a good morphological environment. This invention creates a randomly orientated three-dimensional surface micro texture, tailored to the dimension of the cell type of interest, to increase cell adhesion, cell density, and thus cell growth.

As described above, cell growth can be enhanced by several methods, such as chemically coating the plates. To determine whether cell adhesion and growth can be further enhanced by using the inventive base plate (or substrate) quantitative analysis of cell adhesion densities were performed comparing the inventive diffuser plates to prior art plates, both non-coated and coated.

To test for cell adherence, three different microplates were used: (1) diffuser plates, (2) non-coated Dynatek prior art plates, and (3) collagen coated Falcon prior art plates. Each group was performed in triplicate according to standard procedures as set forth, for example, in Ausubel, F. M., Brent, R., Kingston, R. E. et. al. (eds): "Short Protocols in Molecular Biology", John Wiley & Sons, Inc. pp. 11-9 to 11-10, 1995, and Diamond, M. S., Staunton, D. E., Marlin, S. D.: "Binding of the integrin Mac-1 (CD11b/CD18) to the third immunoglobulin-like domain of ICAM-1 (CD54) and its regulation by glycosylation." Cell, 65(6):961–71, 1991.

Using the above procedure, qualitative results growing osteosarcoma cells were obtained using the following microplates: (1) diffuser plates, (2) non-coated Dynatek prior art plates, and (3) collagen coated Falcon prior art plates. The results demonstrated that the cells grown on the non-coated microplates had poor adhesion and exhibited a round-shaped morphology. Additionally, on non-coated plates, cells tended to adhere to each other (cell-cell clumping) as opposed to adhering to the substrate. In contrast, cells on the chemically coated plates had better adhesion than cells on the non-treated microplates and exhibited a more normal morphology than cells on the non-treated microplates. Additionally, the cells on the chemically coated plates adhered to the substrate, reducing cell-cell clumping. Cells on the non-coated diffuser plates had the best adhesion and exhibited morphology most similar to the morphology exhibited by the cells on the coated plates. Additionally, the cells on the diffuser plates adhered to the substrate, with minimal cell-cell clumping. In sum, as demonstrated by examining the cells under a 700 power microscope, cells on the diffuser plates had the most adhesion and a morphology similar to cells on coated plates, with cell-cell clumping minimized or eliminated.

Figure 4:
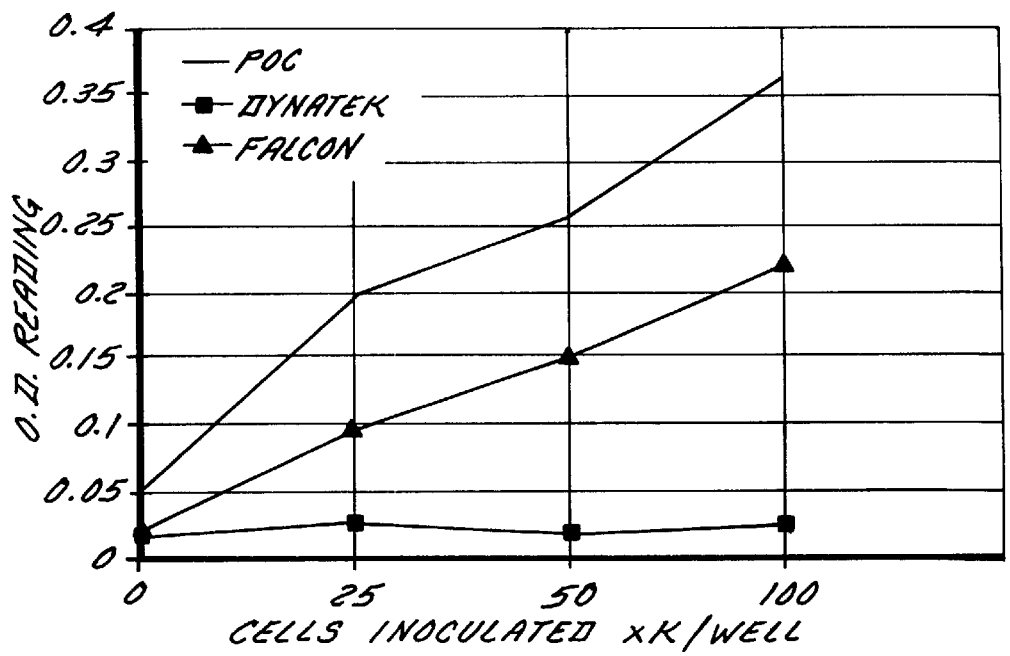
FIG. 4 is a graph of test results comparing results from the use of a microtiter base plate in accordance with the principles of this invention with the results using prior art microplates.

Quantitative analyses show that the inventive diffuser plates have an 8.1 to 16.7 times higher cell adhesion density than that of the prior art non-coated plate. The morphological observations confirm that the cell adhesion density is much higher with the diffuser plates than with both the non-coated and the coated prior art plates. Additionally, analysis show that the inventive diffuser plates have a 1.6 to 2.1 times higher cell adhesion density than that of the prior art coated plate, depending upon the plate's vendor. An example of results obtained from a quantitative analysis is shown in FIG. 4.

Because of the three-dimensional structure, a large surface area can be created in a small area. That is, a three-dimensional microstructure substrate has a larger surface area than a two dimensional planar substrate. A series of ELISA experiments were performed to demonstrate that this property can enhance the signals obtained from immunological and other assays.

Microplates used were flat Dynatek non-coated, Corning coated, Falcon coated, and a plate in accordance with the principles of this invention.

The primary antibody was coated into the microplates by adding 100 microliters of primary antibody (at 1:1000) to each well. The plates were processed identically according to well established procedures.

Optical densities (ODs) were taken for sixteen different wells on each plate. These ODs were then averaged, resulting in the following readings: (1) just over 0.2 for the flat Dynatek non-coated plate; (2) just over 0.3 for the Corning-CoStar coated plate; (3) 0.4 for the Falcon coated plate, and (4) just over 0.5 for the inventive plate. As shown in FIG. 4, the inventive microplates had the highest OD, with over a twenty percent increase over the next best plate, the Falcon coated plate. These data show that more antibody adhered to the inventive plate than to any of the three other plates that were tested. Having a strongly adhered antibody in an ELISA test is important because the antibody forms the basis of the assay. The antibody specifically reacts with an antigen of interest. Thus, more antibody that is bound to a substrate, the more sensitive the assay.

The optical reading for the inventive plates was 0.515±0.1, while the prior art plates of different brands had the following optical readings: 0.211±0.09 for the Dynatek non-coated plate, 0.318±0.06 for the Corning-CoStar plate, and 0.399±0.1 for the Falcon plates. Thus, the sensitivity of the ELISA performed using the diffuser plate had 2.4-, 1.6-, and 1.3- fold increases in performance over the various prior art plates.

When biological molecules are applied to the inventive three-dimensional structure, the adhesion of the molecules to the substrate is increased because the three-dimensional structure increases the substrate's surface area. Thus, more molecules can adhere to the three-dimensional structure than to a two-dimensional planar structure of prior art substrates. Therefore, the inventive three-dimensional structure is an improved substrate for bioassays. Because more molecules bind to the three-dimensional structure of the diffuser plates, more molecules will be available for the bioassay, making bioassays performed on the inventive plates more sensitive than bioassays performed on traditional two-dimensional plates.

Figure 5:
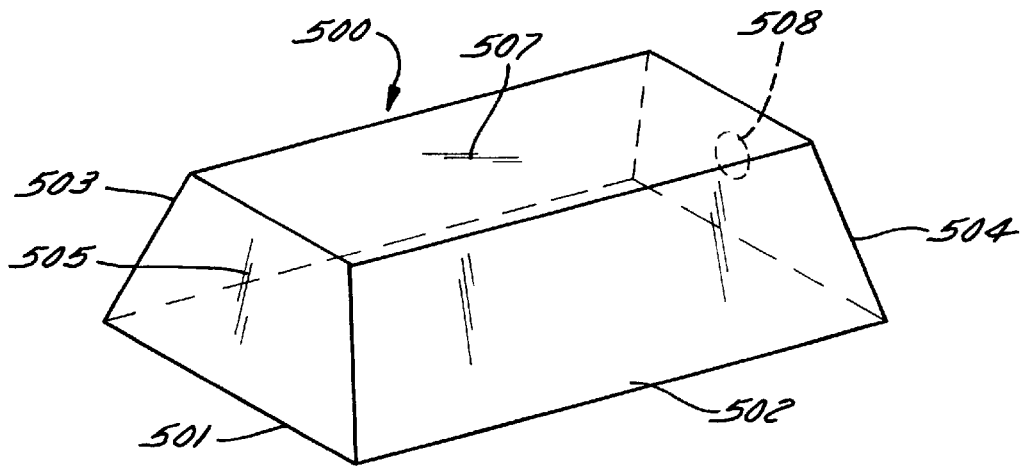
FIG. 5 is an alternative embodiment in accordance with the principals of this invention.

FIG. 5 is a perspective view of an alternative embodiment of this invention. The figure shows a flask 500. Flask 500 is a common apparatus for immunologic testing and comprises an enclosure defined by base plate 501, side walls 502 and 503 and end walls 504 and 505. The flask also includes a top 507 (which may or may not be removable). If top 507 is attached, an inlet 508 is provided for introducing materials into the flask.

In accordance with the principles of this invention, the surface of base plate is rendered three dimensional in a manner to shape and direct light incident thereto and to increase the surface area as was the case with the microplate of FIGS. 1–3. The use of the flask, as well as the case with the microplate, is exactly the same as prior art like apparatus. The results are much improved.

It is to be understood that any apparatus commonly used for cell cultures or immunological testing is improved by having test surfaces structured in accordance with the principles of this invention as measured by any commonly accepted procedure. Test results are obtained in response to light directed from a light source (i.e., 600 of FIG. 1) at the inventive base plate in the conventional manner.

What is claimed is:

1. Apparatus for analyzing biological samples, said apparatus comprising a container having a base plate and side walls for forming a receptacle for said sample, said base plate having a first surface for receiving a sample, said surface having a distribution of features operative to redirect light incident thereto into a controlled pattern with smooth brightness variation.

2. Apparatus as in claim 1 wherein said features have a distribution of features over said first surface and have a feature size about equal to the mean size of cells cultured therein.

3. Apparatus as in claim 1 including an array of upstanding wells connected to said first surface, each of said wells exposing a portion of said surface at the bottom thereof.

4. Apparatus as in claim 3 for the culturing of cells therein, said first surface having a distribution of features having a feature size about equal to the mean cell size of cells cultured therein.

5. Apparatus as in claim 2 wherein said features have height to width ratios in the range of about 1:1 to 1:3.

6. Apparatus as in claim 3 wherein said features have a height to width ration in a range of about 1:1 to 1:3.

7. Apparatus as in claim 4 wherein said base is transparent.

8. Apparatus as in claim 1 wherein said features are distributed randomly.

9. Apparatus for analyzing biological samples, said apparatus comprising a container having a base plate and side walls for forming a receptacle for said sample, said base plate having a first surface for receiving a sample, said surface having a random distribution of features having lateral dimensions about equal to the mean size of cells to be cultured therein.

10. Apparatus as in claim 9 wherein said features are of a shape to redirect light incident thereto into a controlled pattern with smooth brightness variation.

11. Apparatus as in claim 9 including an array of upstanding wells connected to said first surface, each of said wells exposing a portion of said surface at the bottom of thereof.

12. Apparatus as in claim 11 wherein said features have height to width ratios of about 1:1 to 1:3.

* * * * *